United States Patent [19]

Markusch et al.

[11] Patent Number: 4,855,490

[45] Date of Patent: * Aug. 8, 1989

[54] LIQUID POLYISOCYANATE ADDUCT MIXTURES POSSESSING GOOD COMPATIBILITY WITH APOLAR SOLVENTS

[75] Inventors: Peter Markusch, McMurray; George A. Hudson, deceased, late of Pittsburgh, both of Pa., by Richard L. White, administrator

[73] Assignee: Mobay Corporation, Pittsburgh, Pa.

[*] Notice: The portion of the term of this patent subsequent to Oct. 19, 1999 has been disclaimed.

[21] Appl. No.: 262,370

[22] Filed: Oct. 25, 1988

Related U.S. Application Data

[63] Continuation of Ser. No. 389,732, Jun. 18, 1982, abandoned, which is a continuation-in-part of Ser. No. 282,284, Jul. 10, 1987, abandoned.

[51] Int. Cl.$^4$ .................... C07C 127/24; C08G 18/78
[52] U.S. Cl. .................... 560/355; 560/330; 560/335; 560/357; 525/127; 528/59
[58] Field of Search ............... 560/335, 330, 355, 357

[56] References Cited

U.S. PATENT DOCUMENTS

| | | | |
|---|---|---|---|
| 3,124,605 | 3/1964 | Wagner | 260/453 |
| 3,201,372 | 8/1965 | Wagner | 260/77.5 |
| 3,789,037 | 1/1974 | Miller | 260/16 |
| 4,355,138 | 10/1982 | Markusch et al. | 525/127 |
| 4,419,293 | 12/1983 | Hudson et al. | 260/453 |

OTHER PUBLICATIONS

Polyurethanes: Chemistry & Technology, vol. II Technology, Saunders & Frisch, 1964, pp. 468–477.

*Primary Examiner*—Alan Siegel
*Attorney, Agent, or Firm*—Gene Harsh; Joseph C. Gil; Thomas W. Roy

[57] ABSTRACT

The present invention relates to a polyisocyanate adduct mixture which at a 100% solids concentration has an isocyanate content of about 4 to 19 weight percent and is liquid at room temperature. The adduct mixture is prepared from a biuret-containing polyisocyanate and a monohydroxy alcohol which contains 11 to 36 carbon atoms. The adduct mixture possesses good storage stability in common polyisocyanate solvents and good compatibility with apolar solvents. The present invention also relates to the use of the liquid polyisocyante adduct mixture in the process of curing alkyd or acrylic resins and to compositions containing the adduct mixture and alkyd or acrylic resins.

16 Claims, No Drawings

4,855,490

LIQUID POLYISOCYANATE ADDUCT MIXTURES POSSESSING GOOD COMPATIBILITY WITH APOLAR SOLVENTS

This application is a continuation, of application Ser. No. 06/389,732 filed June 18, 1982, now abandoned which is a continuation-in part of application Ser. No. 282,284 filed July 10, 1981, now abandoned.

FIELD OF THE INVENTION

This invention relates to liquid biuret-containing polyisocyanate adduct mixtures which have good compatibility with apolar solvents and good storage stability in solution.

BACKGROUND OF THE INVENTION

It is well known that isocyanates may be added to isocyanate-reactive systems such as alkyd resins or acrylic resins to improve both the curing behavior and the properties of the cured coating. The preparation and use of urethane oils of this type are extensively discussed at pages 468 to 477 of Polyurethanes: Chemistry and Technology, Volume II Technology, Saunders and Frisch, Interscience 1964. It is also known that castings prepared from aliphatic isocyanates impart superior light stability (resistance to yellowing, particularly on exposure to sunlight) as compared to aromatic isocyanates. A class of isocyanates which has been found to be particularly favorable for coating applications are the biuret-containing aliphatic or cycloaliphatic polyisocyanates, especially the tris (isocyanato alkane) biurets such as those disclosed in U.S. Pat. No. 3,124,605 and 3,201,372. It has been found desirable to add such isocyanates to alkyd resin systems containing aliphatic solvents such as those used in the auto refinishing industry. Unfortunately, while these biuret-containing polyisocyanates, including the popular tris (isocyanato alkane) biurets, exhibit some degree of compatibility with the alkyd resins themselves, they display a high degree of incompatibility with apolar solvents normally used in such systems. Since these solvents are both effective and economical in such systems, it was felt that the compatibility of the aliphatic, biuret-containing polyisocyanates would have to be improved if they were to find practical utility in these systems.

In order to improve the compatibility of aliphatic biuret isocyanates with apolar solvents, it was proposed in a copending application, U.S. Ser. No, 282,206 filed July 10, 1981, now U.S. Pat. No. 4,419,293, to react these isocyanates with aliphatic or cycloaliphatic monohydroxy alcohols containing at least 8 carbon atoms. While these modified isocyanates exhibited increased compatibility with apolar solvents, they no longer formed storage stable solutions in the polar solvents normally used to lower the viscosity of isocyanates, since the isocyanate solvents are more polar than apolar solvents used with the isocyanate-reactive systems.

In a copending application, U.S. Ser. No. 282,285 filed July 10, 1981, now U.S. Pat. No. 4,355,138, polyisocyanate adducts were obtained which possessed good compatibility with apolar solvents and good storage stability in common isocyanate solvents. These adducts were formed by reacting polyisocyanates with a monohydroxy compound containing a saturated hydrocarbon chain and a monohydroxy compound containing one or more polarity-inducing groups. Alternatively, the adducts were formed from a monohydroxy compound which contained both a saturated hydrocarbon chain and a polarity-inducing group.

It is an object of the present invention to form additional biuret-containing polyisocyanate adducts which are compatible with apolar solvents and still maintain good storage stability in solution.

It is a further object of the present invention to provide biuret-containing polyisocyanate adducts which overcome the prior art problems associated with the use of isocyanates in isocyanate-reactive systems, such as alkyd resins or acrylic resins.

These objectives may be achieved in accordance with the present invention by forming polyisocyanate adduct mixtures which are liquid at room temperature. Surprisingly, these adduct mixtures possess good storage stability and also good compatibility with apolar solvents.

SUMMARY OF THE INVENTION

The present invention is directed to a polyisocyanate adduct mixture which at a 100% solids concentration has an isocyanate content of about 4 to 19 weight percent and is liquid at room temperature, and comprises the reaction product of (a) a biuret-containing polyisocyanate of the formula

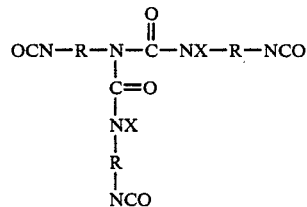

wherein
R represents an aliphatic residue containing 4 to 12 carbon atoms and
X represents H or

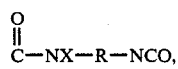

with
(b) about 0.05 to 0.5 moles per equivalent of isocyanate of a saturated, straight or branched monohydroxy alcohol which contains 11 to 36 carbon atoms, or mixtures thereof.

The present invention is also directed to the use of the liquid polyisocyanate adduct mixture in the process of curing alkyd or acrylic resins and to compositions containing these adduct mixtures and alkyd or acrylic resins.

DETAILED DESCRIPTION OF THE INVENTION

The biuret-containing polyisocyanates to be used in accordance with the present invention are represented by the formula

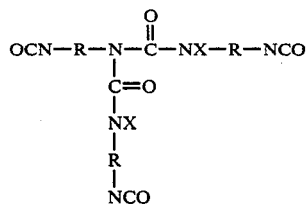

wherein
R represents an aliphatic residue containing 4 to 12 carbon atoms and
X represents H or

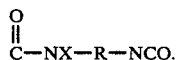

The aliphatic residue R may be linear or may optionally be substituted with alkyl or alkoxy groups. Preferably R contains 4 to 9 carbon atoms, and most preferably R is equivalent to $(CH_2)_6$. These polyisocyanates may be prepared by methods well known to those skilled in the art. Suitable methods are described in U.S. Pat. Nos. 3,124,605; 3,358,010; 3,903,127 and 4,051,165, all of which are herein incorporated by reference.

The liquid polyisocyanate adduct mixtures of the present invention are prepared by reacting the previously described biuret-containing polyisocyanates with monohydroxy alcohols which contain 11 to 36, preferably 12 to 30 carbon atoms. The alcohols are saturated and may contain straight or branched hydrocarbon chains. Any alcohol which meets these requirements may be used provided that the polyisocyanate adduct mixture which is produced is liquid at room temperature at a 100% solids concentration, i.e. in the absence of solvents.

Included among the alcohols which lead to the formation of liquid adduct mixtures are the following.

(1) Alcohols which are liquid at room temperature normally lead to the production of liquid adduct mixtures.

(2) Alcohols which are solid at room temperature can occasionally be mixed to produce a mixture which is liquid at room temperature. For example, mixtures of $C_{12}$ to $C_{15}$ linear primary alcohols may be liquid at room temperature even though individually they are solid or semi-solid at room temperature.

(3) The use of branching in the hydrocarbon chain of the alcohol can result in an alcohol which is liquid at room temperature. For example, a linear $C_{26}$ primary alcohol is solid at room temperature; however, a branched $C_{26}$ primary alcohol may be liquid at room temperature.

It is important to note that the alcohols do not have to be liquid at room temperature. Any saturated, monohydroxy alcohol which contains 11 to 36 carbon atoms and results in the formation of liquid polyisocyanate adduct mixtures may be used in accordance with the present invention.

The proportions of the reactants are chosen to provide about 0.0 to 0.5 moles, preferably about 0.1 to 0.3 moles and most preferably about 0.2 to 0.3 moles of the monohydroxy alcohol per equivalent of isocyanate. The liquid adduct mixture at a 100% solids concentration should have an isocyanate content of about 4 to 19 weight percent, preferably about 5 to 15 weight percent and most preferably about 8 to 13 weight percent.

The biuret-containing polyisocyanate and the monohydroxy alcohol may be reacted under any thermal and catalytic conditions which give rise to the formation of urethane bonds. The temperature should be sufficiently high to effect reaction within commercially acceptable times, but low enough to avoid significant degradation of the polyisocyanate or the modifiers such as by destruction of the biuret bonds of the polyisocyanate. Suitable reaction conditions including temperatures and catalysts are well known to those skilled in the art and a useful compilation is contained in Polyurethanes: Chemistry and Technology, Volume I, Chemistry, Saunders and Frisch, Interscience, 1962.

The polyisocyanate adduct may be formed in the presence of any of the catalysts known to promote hydroxyl-isocyanate reactions. A number of suitable catalysts are discussed at pages 161 to 173 of Polyurethanes: Chemistry and Technology, Volume I. Some suitable catalysts and other reaction conditions for reacting hydroxyl-bearing compounds and biuretcontaining polyisocyanates are discussed in U.S. Pat. No. 3,201,372, incorporated herein by reference.

The most preferred embodiment is to conduct the polyisocyanate addition reaction at ambient temperatures or above in the absence of any catalysts, e.g. room temperature to about 70° C. The absence of catalysts avoids the necessity of subsequently inactivating the catalyst.

The modified polyisocyanate adduct may be formed in substance or in the presence of suitable solvents. Suitable solvents should be inert to isocyanate groups, i.e., they should not contain any hydrogen groups readily reactive with NCO groups. However, it is preferred to conduct at least a portion of the reaction in the absence of solvents in order to determine if a liquid product is formed.

The adduct mixture may also be prepared by reacting the monohydroxy alcohol with the diisocyanate used to form the biuret-containing polyisocyanate either before or during formation of the biuret. However, it is preferred to form the adduct after formation of the biuret-containing polyisocyanate. The order of addition for the reactants is not critical. For example, the monohydroxy alcohol may be added to the polyisocyanate or vice-versa, or the components may be mixed simultaneously.

The relative compatibility of the adduct mixtures of the present invention with apolar solvents is determined by dissolving the adduct mixture in a conventional isocyanate solvent and subsequently titrating an apolar solvent into the solution until some precipitation occurs, normally indicated by cloudiness. For determining the relative compatibility between different polyisocyanate adduct mixtures, the isocyanate solvent may be any solvent in which the polyisocyanate adduct mixture has a reasonable degree of solubility. Among the more common suitable solvents are cellosolve acetate, xylene, methyethylketone, and the like. Of particular interest are those solvent systems which have less than 20 percent by volume of photochemically reactive solvents and particularly those which meet the standards of Rule 66 of California's air pollution code. The particular solvent system in which the compatibility test is performed is felt to have some effect on the results but not on the relative rankings of polyisocyanates tested, i.e. a more compatible polyisocyanate will remain so regardless of the solvent system, although its absolute compatibility may change. The titrant may be any apolar solvent miscible with the solvent system. Of particular interest are those apolar solvents typically used with alkyd resins such as aliphatic solvents. Among these are naphtha, hexane, heptane, and mineral spirits.

In order to determine the storage stability of the polyisocyanate adducts mixture when in solution in common polyisocyanate solvents, samples are subjected to the Cold Cycle Test (CCT). To conduct this test, the samples are cooled to $-20°$ C. for a period of twelve hours and then allowed to warm to room temperature. This test is repeated three times. As the samples warm to room temperature following the third cold cycle, they should become clear. If they remain cloudy, they have not passed the Cold Cycle Test. Any cloudiness can be removed by heating to $60°$ C. to $70°$ C. for a short period of time; however, samples which require this additional heating to become clear, have not passed the test. Good storage stability may be achieved when polyisocyanate adduct mixtures dissolved in xylene at a 40 weight percent solids content are capable of passing the Cold Cycle Test.

In the examples which follow, adducts were prepared from DES N 100 (a commercially available biuret of hexamethylene diisocyanate prepared in accordance with U.S. Pat. No. 3,903,127) and various monohydroxy alcohols. The polyisocyanate was first introduced into the reaction vessel and then the monohydroxy alcohol was added dropwise with stirring at room temperature. After the addition of the alcohol was complete and while maintaining stirring, the mixture was heated to between $60°$ and $70°$ C. for three hours. After completion of the reaction, the mixture was cooled to room temperature. Xylene was then added until a 40 weight percent solids content was obtained. The previously discussed Cold Cycle Test was then conducted.

The compatibility of the adduct mixtures with apolar solvents was then determined by titrating heptane into solutions of the polyisocyanate adduct mixture in xylene (the Heptane Tolerance Test). Heptane was chosen as the titrant because it is readily available in reagent purity and it is believed to be fairly representative of apolar solvents. All tests were conducted with the polyisocyanate adduct mixtures at a 40 weight percent solids content using 50 g specimens. Good compatibility of these adduct mixtures with apolar solvents may be obtained when the amount of heptane titrated, before a 40 weight percent solution of the adduct mixture in xylene turns cloudy, is greater than or equal to 6 ml, however, amounts greater than about 9 ml are preferred with amounts greater than about 15 ml being most preferred. Subsequent testing with commercially available alkyd systems (resin and solvents) verified the compatibility results of the heptane titrations.

Especially preferred monohydroxy alcohols are those which achieve Heptane Tolerance values in accordance with the previously described test of at least 9 ml, preferably at least 12 ml, when reacted to form adducts at a ratio of 0.2 moles of the alcohol per equivalent of isocyanate. This is not to say that the alcohols can only be used in this amount, but merely that when they are used in this amount, they achieve these Heptane Tolerance values. These especially preferred monohydroxy alcohols should also be able to pass the Cold Cycle Test when used to prepare adducts at a ratio of 0.2 moles of the alcohol per equivalent of isocyanate.

The following Table sets forth the monohydroxy alcohol, the number of equivalents of the modifier based on 1 equivalent weight of the biuret (approximately 195 g), whether the mixture passed the Cold Cycle Test (CCT) and the amount of heptane titrated in milliliters before the mixture turned cloudy in accordance with the Heptane Tolerance Test (HTT).

TABLE

| EXAMPLE | ALCOHOL | EQUIVALENTS | CCT | HTT (ml) |
|---|---|---|---|---|
| 1 | Standamul ® GT-16[1] | .20 | Pass | 11.6 |
| 2 | Standamul ® GT-16 | .22 | Pass | 10.6 |
| 3 | Standamul ® GT-16 | .24 | Pass | 13.0 |
| 4 | Standamul ® GT-16 | .26 | Pass | 13.8 |
| 5 | Standamul ® GT-16 | .28 | Pass | 16.0 |
| 6 | Standamul ® GT-16 | .30 | Pass | 18.4 |
| 7 | Standamul ® GT-20[2] | .20 | Pass | 10.6 |
| 8 | Standamul ® GT-20 | .22 | Pass | 10.2 |
| 9 | Standamul ® GT-20 | .24 | Pass | 12.0 |
| 10 | Standamul ® GT-20 | .26 | Pass | 11.2 |
| 11 | Standamul ® GT-20 | .28 | Pass | 10.0 |
| 12 | Standamul ® GT-20 | .30 | Pass | 16.0 |
| 13 | Standamul ® GT-1620[3] | .20 | Pass | 12.0 |
| 14 | Standamul ® GT-1620 | .22 | Pass | 11.2 |
| 15 | Standamul ® GT-1620 | .24 | Pass | 12.0 |
| 16 | Standamul ® GT-1620 | .26 | Pass | 14.6 |
| 17 | Standamul ® GT-1620 | .28 | Pass | 8.0 |
| 18 | Standamul ® GT-1620 | .30 | Pass | 16.4 |
| 19 | Standamul ® GTO-26[4] | .123 | Pass | 6.2 |
| 20 | Standamul ® GTO-26 | .20 | Pass | 8.8 |
| 21 | Standamul ® GTO-26 | .25 | Pass | 11.3 |
| 22 | Standamul ® GTO-26 | .30 | Pass | 13.8 |
| 23 | Standamul ® GTO-26 | .30 | Pass | 13.0 |
| 24 | Neodol ® 23[5] | .20 | Pass | 10.0 |
| 25 | Neodol ® 23 | .30 | Pass | 15.0 |
| 26 | Neodol ® 25[6] | .20 | Pass | 10.0 |
| 27 | Neodol ® 25 | .30 | Pass | 17.0 |

TABLE-continued

| EXAMPLE | ALCOHOL | EQUIVALENTS | CCT | HTT (ml) |
|---|---|---|---|---|
| 28 | 2,6,8-Trimethylnonanol-4 | .10 | Pass | 6.7 |

[1] A registered trademark of Henkel, GT-16 is a branched chain primary alcohol containing 16 carbons and having a specific gravity (25° C.) of 0.840, a hydroxyl number of 218 and a viscosity (25° C.) of 50 cPs.

[2] A registered trademark of Henkel, GT-20 is a branched chain primary alcohol containing 20 carbons and having a specific gravity (25° C.) of 0.835, a hydroxyl number of 180 and a viscosity (25° C.) of 40 cPs.

[3] A registered trademark of Henkel, GT-1620 is a branched chain primary alcohol containing 16–20 carbons and having a specific gravity (25° C.) of 0.847, a hydroxyl number of 192 and a viscosity (25° C.) of 55 cPs.

[4] A registered trademark of Henkel, GTO-26 is a branched chain primary alcohol containing 26 carbons and having a specific gravity (25° C.) of 0.855, a hydroxyl number of 142 and a viscosity (25° C.) of 316 cPs.

[5] A registered trademark of Shell, Neodol ® 23 is a mixture of $C_{12}$ and $C_{13}$ linear primary alcohols having an average molecular weight of 197, a hydroxyl number of 288 and a melting point of 21–22° C.

[6] A registered trademark of Shell, Neodol ® 25 is a mixture of $C_{12}$ to $C_{15}$ linear primary alcohols having an average molecular weight of 221, a hydroxyl number of 256 and a melting point of 22–23° C.

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A polyisocyanate adduct mixture which at a solids concentration has an isocyanate content of about 4 to 19 weight percent and is liquid at room temperature, and comprises the reaction product of
(a) a biuret-containing polyisocyanate of the formula

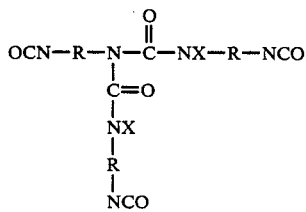

wherein
R represents an aliphatic residue containing 4 to 12 carbon atoms and
X represents H or

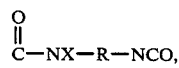

with
(b) about 0.05 to 0.5 moles per equivalent of isocyanate of a saturated, straight or branched monohydroxy alcohol with the exception of 2,6, 8-trimethylnonanol-4 which contains 11 to 36 carbon atoms, or a mixture of said monohydroxy alcohols.

2. The polyisocyanate adduct mixture of claim 1 wherein R represents $(CH_2)_6$.

3. The polyisocyanate adduct mixture of claim 1 or claim 2 wherein component (b) is present in about 0.1 to 0.3 moles per equivalent of isocyanate.

4. The polyisocyanate adduct mixture of claim 1 or 2 wherein the isocyanate content of said adduct mixture is about 5 to 15 weight percent at a 100% solids concentration.

5. The polyisocyanate adduct mixture of claim 1 or 2 wherein component (b) contains 12 to 30 carbon atoms.

6. The polyisocyanate adduct mixture of claim 1 or 2 wherein component (b) is a branched, primary alcohol containing 16 to 20 carbon atoms.

7. The polyisocyanate adduct mixture of claim 1 or 2 wherein component (b) is a branched, primary alcohol containing 26 carbon atoms.

8. The polyisocyanate adduct mixture of claim 1 or 2 wherein component (b) is a mixture of linear, primary alcohols containing 12 to 15 carbon atoms.

9. The polyisocyanate adduct mixture of claim 1 or 2 wherein component (b) is a mixture of linear, primary alcohols containing 12 to 13 carbon atoms.

10. The polyisocyanate adduct mixture of claim 2 wherein said monohydroxy alcohol is selected from those which achieve Heptane Tolerance values of at least 9 ml and pass the Cold Cycle Test when reacted to form said polyisocyanate adduct at a ratio of 0.2 moles of said alcohol per equivalent of isocyanate.

11. A polyisocyanate adduct mixture which at a 100% solids concentration has an isocyanate content of about 8 to 13 weight percent and is liquid at room temperature, and comprises the reaction product of
(a) a biuret-containing polyisocyanate of the formula

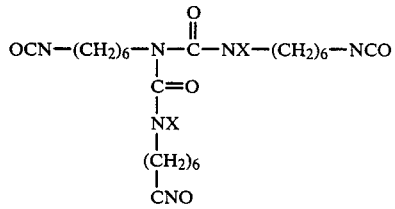

wherein
X represents H or

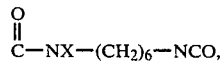

with
(b) about 0.1 to 0.3 moles per equivalent of isocyanate of a saturated, monohydroxy alcohol comprising a member selected from the group consisting of linear, primary alcohols containing 12 to 15 carbon atoms, branched, primary alcohols containing 16 to 20 carbon atoms and branched, primary alcohols containing 26 carbon atoms.

12. The polyisocyanate adduct mixture of claim 11 wherein component (b) is present in about 0.2 to 0.3 moles per equivalent of isocyanate.

13. A polyisocyanate adduct mixture which at a 100% solids concentration has an isocyanate content of about 5 to 15 weight percent and is liquid at room temperature and comprises the reaction product of (a) a biuret-containing polyisocyanate of the formula

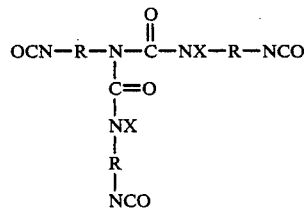

wherein

R represents an aliphatic residue containing 4 to 12 carbon atoms and

X represents H or

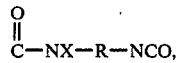

with (b) about 0.2 to 0.3 moles per equivalent of isocyanate of a 2,6,8-trimethylnonanol-4.

14. The polyisocyanate adduct mixture of claim 13 wherein R represents $(CH_2)_6$.

15. The polyisocyanate adduct mixture of claim 1 or 2 wherein said mixture possesses good compatibility with apolar solvents and good storage stability in solution in polyisocyanate solvents.

16. The polyisocyanate adduct mixture of claim 10 or 11 wherein said mixture possesses good compatibility with apolar solvents and good storage stability in solution in polyisocyanate solvents.

* * * * *